US010646550B2

(12) United States Patent
Bullens et al.

(10) Patent No.: US 10,646,550 B2
(45) Date of Patent: May 12, 2020

(54) USE OF C-TYPE NATRIURETIC PEPTIDE VARIANTS TO TREAT SKELETAL DYSPLASIA

(71) Applicant: BIOMARIN PHARMACEUTICAL INC., Novato, CA (US)

(72) Inventors: Sherry Bullens, Novato, CA (US); Stuart Bunting, Novato, CA (US); Tianwei Chou, Novato, CA (US); Augustus O. Okhamafe, Concord, CA (US); Christopher P. Price, Munich (DE); Daniel J. Wendt, Novato, CA (US); Clarence Yap, Novato, CA (US)

(73) Assignee: BioMarin Pharmaceutical Inc., Novato, CA (US)

(*) Notice: Subject to any disclaimer, the term of this patent is extended or adjusted under 35 U.S.C. 154(b) by 0 days.

(21) Appl. No.: 15/880,002

(22) Filed: Jan. 25, 2018

(65) Prior Publication Data
US 2018/0207239 A1 Jul. 26, 2018

Related U.S. Application Data

(62) Division of application No. 15/225,355, filed on Aug. 1, 2016, now Pat. No. 9,907,834.

(60) Provisional application No. 62/320,704, filed on Apr. 11, 2016, provisional application No. 62/199,081, filed on Jul. 30, 2015.

(51) Int. Cl.
*A61K 38/22* (2006.01)
*A61K 38/00* (2006.01)
*A61K 38/16* (2006.01)
*A61K 9/19* (2006.01)
*A61K 47/12* (2006.01)
*A61K 47/26* (2006.01)
*A61K 47/18* (2017.01)
*A61K 47/10* (2017.01)
*A61K 9/00* (2006.01)
*A61K 38/17* (2006.01)

(52) U.S. Cl.
CPC ........ *A61K 38/2242* (2013.01); *A61K 9/0019* (2013.01); *A61K 9/19* (2013.01); *A61K 38/1709* (2013.01); *A61K 47/10* (2013.01); *A61K 47/12* (2013.01); *A61K 47/183* (2013.01); *A61K 47/26* (2013.01)

(58) Field of Classification Search
None
See application file for complete search history.

(56) References Cited

U.S. PATENT DOCUMENTS

| 5,352,770 | A | 10/1994 | Matsuo |
| 6,034,231 | A | 3/2000 | Tanaka et al. |
| 7,276,481 | B2 | 10/2007 | Golembo et al. |
| 7,642,243 | B2 | 1/2010 | Nakao et al. |
| 8,198,242 | B2 | 6/2012 | Wendt et al. |
| 8,598,121 | B2 | 12/2013 | Wendt et al. |
| 8,658,373 | B2 | 2/2014 | Wendt et al. |
| 9,266,939 | B2 | 2/2016 | Crine |
| 2010/0297021 | A1 | 11/2010 | Wendt |
| 2012/0316114 | A1 | 12/2012 | Wendt |

FOREIGN PATENT DOCUMENTS

| EP | 0497368 A1 | 8/1992 |
| WO | 9420534 A1 | 9/1994 |
| WO | 02074234 A2 | 9/2002 |
| WO | WO-03/059291 A2 | 7/2003 |
| WO | 2009067639 A2 | 5/2009 |

OTHER PUBLICATIONS

Alfonzo et al., Characterization of a G protein-coupled guanylyl cyclase-B receptor from bovine tracheal smooth muscle, J. Recept. Signal Transduct Res., 26(4):269-97 (2006).
Altschul et al., Basic local alignment search tool, J. Mol. Biol., 215(3):403-10 (1990).
Bartels et al., Mutations in the transmembrane natriuretic peptide receptor NPR-B impair skeletal growth and cause acromesomelic dysplasia, type Maroteaux, Am. J. Hum. Genet., 75(1):27-34 (2004).
Chusho et al., Dwarfism and early death in mice lacking C-type natriuretic peptide, Proc. Natl. Acad. Sci. USA, 98(7):4016-21 (2001).
Feng et al., Progressive sequence alignment as a prerequisite to correct phylogenetic trees, J. Mol. Evol., 25(4):351-60 (1987).
Gardner et al., Molecular biology of the natriuretic peptide system: implications for physiology and hypertension, Hypertension, 49(3):419-26 (2007).
Henikoff et al., Amino acid substitution matrices from protein blocks, Proc. Natl. Acad. Sci. USA, 89(22):10915-9 (1992).
Higgins et al., Fast and sensitive multiple sequence alignments on a microcomputer, Comput. Aool. Biosci., 5(2):151-3 (1989).
Hunt et al., Bioactivity and metabolism of C-type natriuretic peptide in normal man, J. Clin. Endocrinol. Metab., 78(6):1428-35 (1994).
International Search Report and Written Opinion, International Application No. PCT/US2016/044968, dated Nov. 9, 2016.
Karlin et al., Applications and statistics for multiple high-scoring segments in molecular sequences, Proc. Natl. Acad. Sci. USA, 90(12):5873-7 (1993).
Kenny et al., Hydrolysis of human and pig brain natriuretic peptides, urodilatin, C-type natriuretic peptide and some C-receptor ligands by endopeptidase-24.11, Biochem. J., 291 (Pt. 1):83-8 (1993).
Koller et al., Selective activation of the B natriuretic peptide receptor by C-type natriuretic peptide (CNP), Science, 252(5002):120-3 (1991).

(Continued)

*Primary Examiner* — Shulamith H Shafer
(74) *Attorney, Agent, or Firm* — Marshall, Gerstein & Borun LLP

(57) ABSTRACT

The present disclosure provides for use of variants of C-type natriuretic peptide (CNP), and novel pharmaceutical compositions and formulations comprising CNP variant peptides for the treatment of skeletal dysplasias, one or more symptoms of skeletal dysplasias, such as long bone growth or growth velocity, and other disorders having a skeletal dysplasia and/or CNP-associated symptom or component.

13 Claims, No Drawings

Specification includes a Sequence Listing.

(56) References Cited

OTHER PUBLICATIONS

Krejci et al., Interaction of fibroblast growth factor and C-natriuretic peptide signaling in regulation of chondrocyte proliferation and extracellular matrix homeostasis, J. Cell Sci., 118(Pt. 21):5089-100 (2005).
Levin et al., Natriuretic peptides, N Engl J Med., 339:321-8 (1998).
Maack et al., Physiological role of silent receptors of atrial natriuretic factor, Science, 238(4827):675-8 (1987).
Nakao et al., Molecular biology and biochemistry of the natriuretic peptide system I: Natriuretic peptides, J. Hypertens., 10(9):907-12 (1992).
Nakao et al., Molecular biology and biochemistry of the natriuretic peptide system. II: Natriuretic peptide receptors, J. Hypertens., 10(10):1111-4 (1992).
Olney et al., Heterozygous mutations in natriuretic peptide receptor-B (NPR2) are associated with short stature, J. Clin. Endocrinol. Metab., 91(4):1229-32 (2006).
Olney, C-type natriuretic peptide in growth: a new paradigm, Growth Harm. IGF Res., 16 Suppl A: S6-14 (2006).
Sudoh et al., C-type natriuretic peptide (CNP): a new member of natriuretic peptide family identified in porcine brain, Biochem. Biophys. Res. Commun., 168(2):863-70 (1990).
Thompson et al., Clustal W: improving the sensitivity of progressive multiple sequence alignment through sequence weighting, position-specific gap penalties and weight matrix choice, Nucleic Acids Res., 22(22):4673-80 (1994).
Wu et al., Furin-mediated processing of Pro-C-type natriuretic peptide, J. Biol. Chem., 278(28):25847-52 (2003).
Yamashita et al., Concentration of mRNA for the natriuretic peptide receptor-C in hypertrophic chondrocytes of the fetal mouse tibia, J. Biochem., 127(2):177-9 (2000).
Yasoda et al., Overexpression of CNP in chondrocytes rescues achondroplasia through a MAPK-dependent pathway, Nat. Med., 10(1):80-6 (2004).
Yeung et al., Binding of CNP-22 and CNP-53 to cultured mouse astrocytes and effects on cyclic GMP, Peptides, 17(1):101-6 (1996).
Ogawa et al., Effects of phosphate buffer in parenteral drugs on particle formation from glass vials, Chem. Pharm. Bull (Tokyo), 61(5):539-45 (2013).

SEQUENCE LISTING

```
<160> NUMBER OF SEQ ID NOS: 7

<210> SEQ ID NO 1
<211> LENGTH: 37
<212> TYPE: PRT
<213> ORGANISM: Homo sapiens

<400> SEQUENCE: 1

Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Asn
            20                  25                  30
```

Ser Gly Leu Gly Cys
        35

<210> SEQ ID NO 2
<211> LENGTH: 38
<212> TYPE: PRT
<213> ORGANISM: Homo sapiens

<400> SEQUENCE: 2

Met Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 3
<211> LENGTH: 38
<212> TYPE: PRT
<213> ORGANISM: Homo sapiens

<400> SEQUENCE: 3

Pro Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 4
<211> LENGTH: 38
<212> TYPE: PRT
<213> ORGANISM: Homo sapiens

<400> SEQUENCE: 4

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Asn Ser Gly Leu Gly Cys
        35

<210> SEQ ID NO 5
<211> LENGTH: 39
<212> TYPE: PRT
<213> ORGANISM: Homo sapiens

<400> SEQUENCE: 5

Pro Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 6
<211> LENGTH: 39
<212> TYPE: PRT
<213> ORGANISM: Homo sapiens

<400> SEQUENCE: 6

```
Met Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
            35

<210> SEQ ID NO 7
<211> LENGTH: 38
<212> TYPE: PRT
<213> ORGANISM: Homo sapiens

<400> SEQUENCE: 7

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
            35
```

USE OF C-TYPE NATRIURETIC PEPTIDE VARIANTS TO TREAT SKELETAL DYSPLASIA

PRIORITY CLAIM

This application is a divisional of U.S. patent application Ser. No. 15/225,355, filed on Aug. 1, 2016, which claims benefit of provisional patent application No. 62/320,704, filed on Apr. 11, 2016 and provisional patent application No. 62/199,081, filed on Jul. 30, 2015, the contents of which are hereby incorporated by reference in their entireties.

FIELD OF THE DISCLOSURE

The disclosure relates, in general, to the use of variants of C-type natriuretic peptide (CNP) to treat skeletal dysplasias and formulations of CNP variant peptides.

BACKGROUND OF THE DISCLOSURE

The natriuretic peptide family consists of three structurally related peptides: atrial natriuretic peptide (ANP) (Genbank Accession No. NP_006163, for the ANP precursor protein, NPPA), brain natriuretic peptide (BNP) (GenBank Accession No. NP_002512, for the BNP precursor protein, NPPB), and C-type natriuretic peptide (CNP) (Biochem. Biophys. Res. Commun., 168: 863-870 (1990) (GenBank Accession No. NP_077720, for the CNP precursor protein, NPPC) (J. Hypertens., 10: 907-912 (1992)). These small, single chain peptides (ANP, BNP, CNP) have a 17-amino acid loop structure (Levin et al., N. Engl. J. Med., 339: 863-870 (1998)) and have important roles in multiple biological processes. ANP and BNP bind to and activate the natriuretic peptide receptor A (NPR-A), also termed guanalyl cyclase A (GC-A), resulting in higher intracellular cyclic guanosine monophosphate (cGMP) levels. Likewise, CNP interacts with NPR-B (GC-B) to stimulate the generation of cGMP (J. Hypertens., 10: 1111-1114 (1992)). A third type of receptor, NPR-C, binds each of the natriuretic peptides with high affinity and functions primarily to capture the peptides from the extracellular compartment and deposit the peptides into lysosomes, where they are degraded (Science, 238: 675-678 (1987)). ANP and BNP are produced primarily within the muscle cells of the heart, and are believed to have important roles in cardiovascular homeostasis (Science, 252: 120-123 (1991)). CNP is expressed more widely, including in the central nervous system, reproductive tract, bone and endothelium of blood vessels (Hypertension, 49: 419-426 (2007)).

In humans, CNP is initially produced from the natriuretic peptide precursor C (NPPC) gene as a single chain 126-amino acid pre-pro polypeptide (Biochem. Biophys. Res. Commun., 168: 863-870 (1990)). Removal of the signal peptide yields pro-CNP, and further cleavage by the endoprotease furin generates an active 53-amino acid peptide (CNP-53), which is secreted and cleaved again to produce the mature 22-amino acid peptide (CNP-22) (Wu, J. Biol. Chem. 278: 25847-852 (2003)). CNP-53 and CNP-22 differ in their distribution, with CNP-53 predominating in tissues, while CNP-22 is mainly found in plasma and cerebrospinal fluid (J. Alfonzo, Recept. Signal. Transduct. Res., 26: 269-297 (2006)). The predominant CNP form in cartilage is unknown. Both CNP-53 and CNP-22 bind similarly to NPR-B. Furthermore, they both induce cGMP production in a dose-dependent and similar fashion (VT Yeung, Peptides, 17: 101-106 (1996)).

Natural CNP genes and polypeptides have been previously described. U.S. Pat. No. 5,352,770 discloses isolated and purified CNP-22 from porcine brain identical in sequence to human CNP and its use in treating cardiovascular indications. U.S. Pat. No. 6,034,231 discloses the human gene and polypeptide of proCNP (126 amino acids) and the human CNP-53 gene and polypeptide.

Clearance of CNP from the extracellular space occurs through the action of membrane-bound neutral endopeptidase (NEP), which rapidly degrades CNP (Biochem. J., 291 (Pt 1): 83-88 (1993)), and through NPR-C, which binds to and deposits CNP into lysosomes, where CNP is degraded. CNP has been shown to have an in vivo half-life of 2.6 min in the normal human (J. Clin. Endocrinol. Metab., 78: 1428-35 (1994)). The low plasma concentration of CNP (J. Bone Moner. Res., 19 (Suppl.1)S20 (2004)) and its co-expression with NPR-B in a number of tissues suggests that CNP functions primarily through an autocrine/paracrine mechanism.

As stated above, CNP binds to and activates natriuretic peptide receptor B (NPR-B), also termed guanylyl cyclase B (GC-B), resulting in higher intracellular cyclic guanosine monophosphate (cGMP) levels. Downstream signaling mediated by cGMP generation influences a diverse array of biological processes that include endochondral ossification. Accordingly, elevated or depressed levels of any of the components in this pathway may lead to aberrant bone or cartilage growth. For example, knockout of either CNP or NPR-B in mouse models results in animals having a dwarfed phenotype with shorter long bones and vertebrae. Mutations in human NPR-B that block proper CNP signaling have been identified and result in dwarfism (Olney, et al., J. Clin. Endocrinol. Metab. 91(4): 1229-1232 (2006); Bartels, et al., Am. J. Hum. Genet. 75: 27-34 (2004)). In contrast, mice engineered to produce elevated levels of CNP display elongated long bones and vertebrae.

Achondroplasia is a result of an autosomal dominant mutation in the gene for fibroblast growth factor receptor 3 (FGFR-3), which causes an abnormality of cartilage formation. FGFR-3 normally has a negative regulatory effect on chondrocyte growth, and hence bone growth. In achondroplasia, the mutated form of FGFR-3 is constitutively active, which leads to severely shortened bones. Both chondrocyte proliferation and differentiation appear to be disturbed, leading to remarkably short growth plate cartilage (P. Krejci et al., J. Cell Sci. 118: 5089-5100 (2005)). Endochondral ossification is the process that governs longitudinal long-bone growth. There are four zones of the growth plate—resting, proliferative, hypertrophic and zone of calcification. In the growth plate, NPR-B is expressed by proliferative cells while NPR-C is expressed by hypertrophic cells (Yamashite et al., J. Biochem. 127: 177-179 (2000)). In normal endochondral bone growth, chondrocytes organize in columns and proliferate in the proliferative zone of the growth plate. These columns are disorganized in achondroplasia patients. Additionally, the hypertrophic zone is where the cells become large and eventually apoptose (lyse), leading to osteocyte invasion and mineralization. The hypertrophic chondrocytes and the overall size of the zone are much smaller in achondroplasia patients than in normal patients. CNP is an agonist for NPR-B, a positive regulator of chondrocyte and bone growth. Downstream signaling of CNP/NPR-B inhibits the FGFR-3 pathway at the level of mitogen-activated protein kinase (MAP K). Inhibition at MAP K promotes proliferation and differentiation of the chondrocytes in the proliferative and hypertrophic zones of the growth plate, resulting in bone growth.

In humans activating mutations of FGFR-3 are the primary cause of genetic dwarfism. Mice having activated FGFR-3 serve as a model of achondroplasia, the most common form of the skeletal dysplasias, and overexpression of CNP rescues these animals from dwarfism. Accordingly, CNP and functional variants of CNP are potential therapeutics for treatment of the various skeletal dysplasias.

Therapeutic use of CNP is currently limited by its short plasma half-life, which has been shown to be 2.6 minutes in vivo in humans (J Clin. Endocrinol. Metab., 78: 1428-35 (1994)). To increase CNP concentration above intrinsic levels (about 5 pM) typically found in human plasma, continuous infusion has been necessary in all human and animal studies using systemically administered CNP. Two mechanisms by which the half-life of CNP is reduced in human plasma are degradation by neutral endopeptidase (NEP) and clearance by natriuretic peptide receptor C (NPR-C) (Growth Horm. & IGF Res., 16: S6-S14 (2006)). A CNP variant having a longer in vivo serum half-life and exhibiting similar or improved activity to that of wild-type CNP is important for a sustainable therapeutic strategy.

The biological activities of various analogs and derivatives of CNP have been evaluated. See e.g., U.S. Pat. No. 7,276,481, PCT Publication No. WO 94/20534 which discloses a chimera of CNP-22 and the 5-amino acid C-terminus of ANP designated as the vasonatrin peptide (VNP). U.S. Pat. Nos. 8,198,242, and 8,598,121 disclose use of CNP variants to treat skeletal dysplasias, such as achondroplasia. U.S. Pat. Nos. 7,642,243 and 8,658,373 describe use of variants of CNP-22 or CNP-53 to treat arthritis.

SUMMARY OF THE DISCLOSURE

The present disclosure relates to use of CNP variant peptides to treat skeletal dysplasias, to treat one or more skeletal dysplasia-associated symptom(s), or to improve one or more consequence(s) or physiological symptom(s) of a skeletal dysplasia in a subject suffering therefrom, when the CNP variant peptide is administered above a certain dose amount and/or under a certain drug administration regime as herein described. It is disclosed herein that administration of CNP variant peptides can lead to improved growth velocity in achondroplasia subjects. In various embodiments, the CNP variant peptide is CNP-38 or Pro-Gly-CNP-37.

In various embodiments, the disclosure provides a method of treating skeletal dysplasia, comprising administering a composition comprising a CNP variant peptide to a subject in need thereof in an amount of at least 7.5 µg/kg, wherein the administering treats a skeletal dysplasia or improves at least one symptom or physiological consequence of the skeletal dysplasia.

In one embodiment, the treatment is an improvement in one or more symptoms of skeletal dysplasia selected from the group consisting of increased absolute growth, improved or increased growth velocity, increased QCT bone mineral density (BMD), improvement in growth plate morphology, increased long-bone growth, improvement in the morphology of the spine, improved or increased elbow joint range of motion and decreased sleep apnea.

In one embodiment, the skeletal dysplasia is selected form the group consisting of achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, chondrodysplasia punctata, camptomelic dysplasia, congenital lethal hypophosphatasia, perinatal lethal type of osteogenesis imperfecta, short-rib polydactyly syndromes, hypochondroplasia, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia. In a preferred embodiment, the skeletal dysplasia is achondroplasia.

Also provided is a method of increasing long bone growth in a subject, comprising administering a composition comprising a CNP variant peptide to a subject in need thereof in an amount of at least 7.5 µg/kg, wherein the administering increases long bone growth. In a preferred embodiment, the subject has achondroplasia.

The disclosure also contemplates a method of enhancing or increasing the velocity of growth (i.e., growth velocity) in a subject, comprising administering a composition comprising a CNP variant peptide to a subject in need thereof in an amount of at least 7.5 µg/kg, wherein the administering enhances or increases growth velocity in the subject. In a preferred embodiment, the subject has achondroplasia. In various embodiments, the enhancement or increase in growth velocity is an increase in annualized growth velocity in the range of 25%-50% change from baseline in the subject. In one embodiment, the enhancement or increase in growth velocity is an increase in annualized growth velocity of at least about 25%, more preferably at least about 40%, change from baseline in the subject.

It is contemplated that the enhancement in growth velocity may be assessed by measuring standing height, sitting height, weight, head circumference, upper arm length, lower arm length, upper leg length, lower leg length, hand length and/or foot length.

In the various methods and compositions described herein, the CNP variant peptide may be selected from the group consisting of:

```
                            [CNP-37(M32N); SEQ ID NO: 1]
    QEHPNARKYKGANKKGLSKGCFGLKLDRIGSNSGLGC;

(Met-CNP-37; SEQ ID NO: 2)
    MQEHPNARKYKGANKKGLSKGCFGLKLDRIGSMSGLGC;

(Pro-CNP-37; SEQ ID NO: 3)
    PQEHPNARKYKGANKKGLSKGCFGLKLDRIGSMSGLGC;

[Gly-CNP-37 (M32N); SEQ ID NO: 4]
    GQEHPNARKYKGANKKGLSKGCFGLKLDRIGSNSGLGC;

(Pro-Gly-CNP-37; SEQ ID NO: 5)
    PGQEHPNARKYKGANKKGLSKGCFGLKLDRIGSMSGLGC;

(Met-Gly-CNP-37; SEQ ID NO: 6)
    MGQEHPNARKYKGANKKGLSKGCFGLKLDRIGSMSGLGC;
    and (Gly-CNP-37 or CNP-38: SEQ ID NO: 7)
    GQEHPNARKYKGANKKGLSKGCFGLKLDRIGSMSGLGC.
```

In various preferred embodiments, the CNP variant peptide is CNP-38 or Pro-Gly-CNP-37.

In the various methods described herein, the amount of CNP variant peptide administered ranges from about 7.5 µg/kg to about 100 µg/kg, preferably about 7.5 µg/kg to about 80 µg/kg, more preferably about 7.5 µg/kg to about 60 µg/kg. In various embodiments, the amount of CNP variant peptide administered is at least about 7.5 µg/kg, at least about 15 µg/kg, at least about 30 µg/kg or at least about 60 µg/kg.

In the various methods described herein, the CNP variant peptide or composition or formulation comprising the same is administered either subcutaneously or parenterally, preferably subcutaneously. It is also contemplated that the CNP variant peptide is administered by other routes. Exemplary routes of administration include, but are not limited to subcutaneous, intraarticular, intravenous, intra-arterial, intraperitoneal, intramuscular, intradermal, intrathecal, intraperitoneal, intramuscular, intradermal, intrathecal, topical, transdermal, or transmucosal administration.

In the various methods described herein, the CNP variant peptide or composition or formulation comprising the same is administered to the subject in a single treatment or in multiple doses. The multiple doses may be administered once daily, or in multiple doses over the course of treatment. In various embodiments, it is contemplated that the CNP variant peptide or composition or formulation comprising the same is administered, in a single dose or in multiple doses, daily, every other day, every 3 days, 2 times per week, 3 times per week, weekly, bi-weekly, every 3 weeks, monthly, every 6 weeks, every 2 months, every 3 months or other as deemed appropriate by a treating physician. In particularly preferred embodiments, the CNP variant peptide or composition or formulation comprising the same is administered to the subject once daily for a period of at least one month, two months, three months, four months, five months, six months, seven months, eight months, nine months, ten months, eleven months, twelve months, or longer.

In certain embodiments of the herein described methods, administration of the CNP variant peptide or composition or formulation comprising the same is adjusted to allow for periods of preventative or therapeutic treatment followed by a recovery period. For example, the CNP variant peptide or composition or formulation comprising the same may be administered intraarticularly, subcutaneously, intravenously, or by another mode daily or multiple times per week for a period of time, followed by a period of no treatment, then the cycle is repeated. In some embodiments, the initial period of treatment (e.g., administration of the CNP variant peptide daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the CNP variant peptide is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

In the various methods described herein, it is preferred that administration of the CNP variant peptide or composition or formulation comprising the same not cause or result in an adverse event in the subject rated as grade two or higher. In other embodiments of the methods described herein, administration of the CNP variant peptide or composition or formulation comprising the same results in no clinically significant change in blood hemoglobin concentration, blood platelet number, blood electrolyte concentration, blood urea nitrogen concentration, blood creatinine concentration, blood alkaline phosphatase concentration, blood alanine amino transferase concentration and/or blood aspartate aminotransferase concentration in said subject.

In the various methods described herein, in preferred embodiments, administration of the CNP variant peptide or composition or formulation comprising the same results in a change in (i) the upper body length to lower body length ratio, (ii) the upper arm length to forearm length ratio, or (iii) the upper leg length to lower leg length ratio, of between about −0.25 and about 0.25, about −0.20 and about 0.20, about −0.15 and about 0.15, about −0.10 and about 0.10, or about −0.05 and about 0.05, compared to baseline (i.e., prior to administration of the CNP variant peptide or composition or formulation comprising the same).

In various embodiments, the disclosure provides for compositions or formulations comprising a CNP variant peptide, or use of a composition or formulation comprising a CNP variant peptide in the methods described herein. In one embodiment, the composition or formulation further comprises a pharmaceutically acceptable excipient, carrier or diluent. In certain embodiments, the composition is prepared from a formulation, either liquid or lyophilized, comprising a citric acid/citrate buffer or an acetic acid/acetate buffer having a pH from about 4 to about 6. In various embodiments, the pH is about 5.5.

Also contemplated is a method of treatment as described herein further comprising administration of a second agent.

In various embodiments, the CNP variant peptides used in the methods and compositions or formulations described herein can be attached to a hydrophobic acid, and can be attached to one or more hydrophobic acids. Non-limiting examples of hydrophobic acids include straight-chain or branched, saturated or unsaturated $C_5$-$C_{12}$ carboxylic acids (e.g., pentanoic acid, heptanoic acid, etc.) and natural fatty acids. The hydrophobic acids can be attached to the N-terminus, the C-terminus, and/or the side chain of one or more amino acid residues. In one embodiment, the hydrophobic acids are conjugated to the N-terminus.

In yet another embodiment, the CNP variant peptides used in the methods and compositions of the present invention are chimera, or fusion proteins, comprising a CNP variant peptide, and a cleavable peptide or protein, or peptide tag. Exemplary cleavable proteins or peptides include, but are not limited to, histidine (e.g., hexa-His) tags; TAF12: human transcription factor TAF12; KSI: ketosteroid isomerase; MBP: maltose-binding protein; β-Gal: β-galactosidase; GST: glutathione-S-transferase; Trx: thioredoxin; CBD: chitin binding domain; BMPM: BMP-2 mutation, SUMO, CAT, TrpE, staphylococcal protein A, streptococcal proteins, starch-binding protein, cellulose-binding domain of endoglucanase A, cellulose-binding domain of exoglucanase Cex, biotin-binding domain, recA, Flag, c-Myc, poly(His), poly(Arg), poly(Asp), poly(Gln), poly(Phe), poly(Cys), green fluorescent protein, red fluorescent protein, yellow fluorescent protein, cyan fluorescent protein, biotin, avidin, streptavidin, antibody epitopes, and fragments thereof.

In various embodiments described herein, the CNP variant peptide may be a monomer or a dimer. In a related embodiment the monomers of dimeric CNP variant peptides can be attached N-terminus to N-terminus via a linker or no linker, N-terminus to C-terminus via a linker or no linker, or C-terminus to C-terminus via a linker or no linker.

In any of the embodiments disclosed herein, the CNP variant peptides may have substantially the same or better biological activity than wild-type CNP-22. For example, the CNP variant peptides may retain at least 50%, 60%, 70%, 80%, 90%, 95% or more of the activity of wild-type CNP-22, or may have greater activity than CNP-22, e.g., with respect to interaction with NPR-B (GC-B) to stimulate the generation of cGMP. Alternatively, or in addition, the CNP variant peptides may retain at least 50%, 60%, 70%, 80%, 90%, 95% or more of the activity of wild-type CNP-22, or may have greater activity than CNP-22, with respect to regulating endochondral bone growth and chondrocyte activity, including but not limited to chondrocyte proliferation, chondrocyte differentiation, inhibition of the mitogen activated protein (MAP) kinase/MEK (Raf-1) kinase signaling pathway, and promoting endochondral ossification. In any of the embodiments described herein, the CNP variant peptides may comprise an amino acid sequence that is at least 40%, 50%, 60%, 70%, 80%, 90%, 95% or more identical or homologous to amino acids 6-22 or 1-22 of wild-type CNP-22.

In various embodiments, the CNP variant peptides can optionally have conjugation(s) or extension(s), e.g., at the N- and/or C-terminus to facilitate cartilage targeting, reduce renal clearance, and/or increase resistance to NEP degradation. Such conjugation(s) or extension(s) can comprise molecules or sequences formed or derived from, e.g., polyAsp, polyGlu, cartilage-targeting peptides, sialoprotein, PEGs, carbohydrates, hydrophobic acids, NPPC or non-CNP (poly) peptides, or combinations thereof.

It is further contemplated that the CNP variant peptides can be conjugated to a hydrophobic polymeric or non-polymeric moiety, such as, e.g., heptanoic acid, pentanoic acid, or fatty acids. The hydrophobic moiety can be conjugated to the side chain of an amino acid residue, including but not limited to a lysine, a serine, a cysteine or a threonine, or can be attached to the N-terminus and/or C-terminus of the CNP variant.

In various embodiments, the CNP variant peptides useful in the methods have a pI in the range from about 8 to about 10.5 or from about 8.5 to about 10.

In various embodiments, the disclosure provides for use of a pharmaceutical composition comprising a CNP variant peptide, optionally another biologically active agent, and optionally a pharmaceutically acceptable excipient, carrier or diluent. In various embodiments, the compositions are sterile pharmaceutical compositions suitable for parenteral injection. In some embodiments, the compositions comprise substantially pure CNP variant peptide, e.g. at least about 90% or 95% pure. In some embodiments, the compositions contain less than about 5%, 4%, 3%, 2%, 1% or 0.5% contaminants, such as other human proteins, porcine proteins, or CNP-53 or fragments thereof (other than the desired CNP variant peptide). In various embodiments, the sterile composition is administered to a subject for treating or preventing a skeletal dysplasia or or one or more symptoms or physiological consequences of a skeletal dysplasia disclosed herein.

CNP variant peptides useful herein advantageously retain CNP activity and exhibit increased serum half-life. Retention of CNP activity can be shown, for example, as retention of desired in vivo biological effect, or retention of at least about 50%, 60%, 70%, 80%, 90%, 95% or at least about 100% of the cGMP stimulating activity of CNP-22, under the same concentration (e.g., 1 μM of CNP peptide or greater than the ED80). In some embodiments, CNP variant peptides exhibit at least about 1.5-fold, 2-fold, 3-fold, 4-fold, 5-fold, 10-fold, 15-fold, 20-fold, 25-fold, 30-fold, 35-fold or 40-fold increase in serum half-life compared to CNP-22.

In a related embodiment, the CNP variant peptides described herein have increased NEP resistance and exhibit increased half-life compared to wild-type CNP-22. In one embodiment, the half-life of the CNP variant peptides is increased by about 20%, 30%, 40%, 50%, 60%, 70%, 80%, 90%, 95%, 96%, 97%, 98%, 99% or about 100% compared to wild-type CNP-22.

Use of any of the foregoing CNP variant peptides, or composition or formulation comprising the same, described herein in preparation of a medicament for treatment of skeletal dysplasia and symptoms or other physiological manifestations described herein associated with skeletal dysplasia is also contemplated. Syringes, e.g., single use or pre-filled syringes, sterile sealed containers, e.g. vials, bottle, vessel, and/or kits or packages comprising any of the foregoing CNP variant peptides, or composition or formulation comprising the same, optionally with suitable instructions for use, are also contemplated.

Also contemplated herein are formulations comprising (a) a CNP variant peptide described herein and (b) one or more components selected from the group consisting of a buffering agent, an isotonicity agent, a stabilizer and an anti-adsorbent agent. In particularly preferred embodiments, buffering agents employed in the formulations may be citric acid monohydrate, sodium citrate dihydrate, or a combination of the two. In yet other preferred embodiments, isotonicity agents employed in the formulations of the present invention may be trehalose dihydrate, D-mannitol, or a combination of the two. In other preferred embodiments, the stabilizer employed in the formulations of the present invention is L-methionine. In yet other preferred embodiments, the anti-adsorbent agent employed in the formulations of the present invention is polysorbate 80.

In various embodiments, the formulations of the present invention are lyophilized, in liquid form, or in liquid form that has been reconstituted from a previously lyophilized form. In certain embodiments, the formulations of the present invention are preservative-free and, optionally, may be contained within a type 1 untreated borosilicate glass vial. Optionally, the formulations of the present invention have a pH in the range of between about 5.0 and about 6.0, preferably about 5.5.

In other embodiments, the formulations of the present invention comprise a CNP variant peptide at a concentration of at least about 2.0 mg/ml, 5.0 mg/ml, 10.0 mg/ml, or higher. In a particularly preferred embodiment, the formulation of the present invention comprises a CNP variant peptide at a concentration of about 10.0 mg/ml. In particularly preferred embodiments, the CNP variant peptide of the formulation is CNP-38 or Pro-Gly-CNP-37.

In other embodiments, the formulations of the present invention comprise a CNP variant peptide as described herein, citric acid monohydrate, sodium citrate dihydrate, trehalose dihydrate, D-mannitol, L-methionine and polysorbate 80. In certain preferred embodiments, the CNP variant peptide is present at a concentration between about 2.0 mg/ml and about 10.0 mg/ml, the citric acid monohydrate is present at a concentration between about 0.15 mg/ml and about 0.40 mg/ml, the sodium citrate dihydrate is present at a concentration between about 0.5 mg/ml and about 1.5 mg/ml, the trehalose dihydrate is present at a concentration between about 30 mg/ml and about 70 mg/ml, the D-mannitol is present at a concentration between about 10 mg/ml and about 20.0 mg/ml, the L-methionine is present at a concentration between about 0.5 mg/ml and about 1.5 mg/ml and the polysorbate 80 is present at a concentration between about 0.01 mg/ml and about 0.1 mg/ml. In a particularly preferred embodiment, the CNP variant is present at a concentration of about 10.0 mg/ml, the citric acid monohydrate is present at a concentration of about 0.28 mg/ml, the sodium citrate dihydrate is present at a concentration of about 1.08 mg/ml, the trehalose dihydrate is present at a concentration of about 58.01 mg/ml, the D-mannitol is present at a concentration of about 15.0 mg/ml, the L-methionine is present at a concentration of about 0.73 mg/ml and the polysorbate 80 is present at a concentration of about 0.05 mg/ml.

The CNP variant peptide-containing formulations described herein are useful and may be employed in the various methods described herein.

It is understood that each feature or embodiment, or combination, described herein is a non-limiting, illustrative example of any of the aspects of the disclosure and, as such, is meant to be combinable with any other feature or embodiment, or combination, described herein. For example, where features are described with language such as "one embodiment", "some embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the disclosure. Where examples of values falling within ranges are disclosed, any of these examples are contemplated as possible endpoints of a range, any and all numeric values between such endpoints are contemplated, and any and all combinations of upper and lower endpoints are envisioned.

DETAILED DESCRIPTION OF THE DISCLOSURE

The present disclosure relates to methods of using CNP variant peptides to treat skeletal dysplasias, one or more symptoms or physiological consequences of skeletal dysplasias and other disorders having a skeletal dysplasia and/or CNP-associated symptom or component. The present disclosure also relates to compositions and formulations comprising a CNP variant peptide and use of such compositions or formulations for treating skeletal dysplasia or a symptom or physiological consequence of a skeletal dysplasia, increasing long bone growth in a subject in need thereof, or improving or increasing growth velocity in a subject in need thereof, for example in a subject suffering from a skeletal dysplasia.

A. Definitions

Unless otherwise stated, the following terms used in this application, including the specification and claims, have the definitions given below.

As used in the specification and the appended claims, the indefinite articles "a" and "an" and the definite article "the" include plural as well as singular referents unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

Definition of standard chemistry terms may be found in reference works, including Carey and Sundberg, Advanced Organic Chemistry, $3^{rd}$ Edition, Vols. A and B (Plenum Press, New York 1992). The practice of the present disclosure may employ, unless otherwise indicated, certain conventional methods of synthetic organic chemistry, mass spectrometry, preparative and analytical chromatography, protein chemistry, biochemistry, recombinant DNA technology and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., $4^{th}$ Edition, 2004); Sambrook, et al., Molecular Cloning: A Laboratory Manual ($2^{nd}$ Edition, 1989); Methods In Enzymology (S. Colowick and N. Kaplan eds., Academic Press, Inc.); Remington's Pharmaceutical Sciences, $18^{th}$ Edition (Easton, Pa.: Mack Publishing Company, 1990).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

Conventional notation is used herein to portray polypeptide and peptide sequences: the left-hand end of a polypeptide or peptide sequence is the amino-terminus; the right-hand end of a polypeptide sequence is the carboxyl-terminus.

In one embodiment, the CNP variant peptides described herein useful in the methods are generated via recombinant means, using a polynucleotide encoding a CNP variant peptide. CNP variant peptides expressed by such polynucleotides may be produced by methods including growing host cells in culture medium under conditions suitable for expression of the polynucleotide encoding a CNP variant, and isolating the expression product from the host cells or culture medium. Actual expression products may vary slightly from the encoded protein product depending on any post-translational processing. Methods for producing the CNP variant peptides of the present invention are disclosed at least in U.S. Pat. No. 8,198,242, incorporated herein by reference.

The terms "identical" and percent "identity", in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially homologous" or "substantially identical", in the context of two nucleic acids or polypeptides, generally refers to two or more sequences or subsequences that have at least 40%, 50%, 60%, 70%, 80%, 90%, 95%, or 98% nucleotide or amino acid residue identity, when compared and aligned for maximum correspondence, as measured using one of the following sequence comparison algorithms or by visual inspection. In certain embodiments, the substantial homology or identity exists over regions of the sequences that are at least about 25, 50, 100 or 150 residues in length. In another embodiment, the sequences are substantially homologous or identical over the entire length of either or both comparison biopolymers.

For sequence comparison, typically one sequence acts as a reference sequence, to which test sequences are compared. When using a sequence comparison algorithm, test and reference sequences are inputted into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math., 2: 482 (1981), by the homology alignment algorithm of Needleman & Wunsch, J. Mol. Biol., 48: 443 (1970), by the search for similarity method of Pearson & Lipman, Proc. Natl. Acad. Sci. USA, 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection. One example of a useful algorithm is PILEUP, which uses a simplification of the progressive alignment method of Feng & Doolittle, J. Mol. Evol., 35: 351-360 (1987) and is similar to the method described by Higgins & Sharp, CABIOS, 5: 151-153 (1989). Another algorithm useful for generating multiple alignments of sequences is Clustal W (Thompson et al., Nucleic Acids Research, 22: 4673-4680 (1994)). An example of an algorithm that is suitable for determining percent sequence identity and sequence similarity is the BLAST algorithm (Altschul et al., J. Mol. Biol., 215: 403-410 (1990); Henikoff & Henikoff, Proc. Natl. Acad. Sci. USA, 89: 10915 (1989); Karlin & Altschul, Proc. Natl. Acad. Sci. USA, 90: 5873-5787 (1993)). Software for performing BLAST analyses is publicly available through the National Center for Biotechnology Information.

"Wild-type" (wt) is a term referring to the natural form, including sequence, of a polynucleotide, polypeptide or protein in a species. A wild-type form is distinguished from a mutant form of a polynucleotide, polypeptide or protein arising from genetic mutation(s).

In one embodiment, a first peptide that is an "analog" or "variant" or "derivative" of a second peptide is a peptide having at least about 50%, 60% or 70% sequence homology, but less than 100% sequence homology, with the second peptide. Such analogs, variants or derivatives may be comprised of non-naturally occurring amino acid residues, including without limitation, homoarginine, ornithine, penicillamine, and norvaline, as well as naturally occurring amino acid residues.

The natriuretic peptide precursor C (NPPC) polypeptide is a single chain 126-amino acid pre-pro polypeptide, and which upon cleavage ultimately results in wild type CNP-22 (wtCNP-22). Removal of the signal peptide from NPPC yields pro-CNP, and further cleavage by the endoprotease furin generates an active 53-amino acid peptide (CNP-53), which is secreted and cleaved again to produce the mature 22-amino acid peptide (CNP, or CNP-22). In one embodiment, a "CNP variant peptide" is at least about 40%, 50%, 60%, 70%, 75%, 80%, 85%, 90%, or 95% homologous to the wild type NPPC over the same number of amino acid residues. It is further contemplated that a CNP variant peptide may comprise from about 1 to about 53, or 1 to 38, or 1 to 37, or 1 to 35, or 1 to 31, or 1 to 27, or 1 to 22, or 10 to 35, or about 15 to about 37 residues of the NPPC polypeptide. In one embodiment, a CNP variant may comprise a sequence of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 amino acids derived from the NPPC polypeptide.

The term "effective amount" means a dosage sufficient to produce a desired result on a health condition, pathology, or disease of a subject or for a diagnostic purpose. The desired result may comprise a subjective or objective improvement in the recipient of the dosage. "Therapeutically effective amount" refers to that amount of an agent effective to produce the intended beneficial effect on health. An appropriate "effective" amount in any individual case may be determined by one of ordinary skill in the art using routine experimentation. It will be understood that the specific dose level and frequency of dosage for any particular patient may be varied and will depend upon a variety of factors, including the activity of the specific compound employed; the bioavailability, metabolic stability, rate of excretion and length of action of that compound; the mode and time of administration of the compound; the age, body weight, general health, sex, and diet of the patient; and the severity of the particular condition.

"Treatment" refers to prophylactic treatment or therapeutic treatment or diagnostic treatment. In certain embodiments, "treatment" refers to administration of a compound or composition to a subject for therapeutic, prophylactic or diagnostic purposes.

A "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional or physical, subjective or objective. The compounds of the disclosure may also be given as a therapeutic treatment or for diagnosis.

"Pharmaceutical composition" or "formulation" refers to a composition suitable for pharmaceutical use in subject animal, including humans and mammals. A pharmaceutical composition comprises a therapeutically effective amount of a CNP variant peptide, optionally another biologically active agent, and optionally a pharmaceutically acceptable excipient, carrier or diluent. In an embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use, including but not limited to metal salts (e.g., sodium, potassium, magnesium, calcium, etc.) and salts of ammonia or organic amines.

By "pharmaceutically acceptable" or "pharmacologically acceptable" is meant a material that is not biologically or otherwise undesirable, i.e., the material may be administered to an individual without causing any undesirable biological effects or without interacting in a deleterious manner with any of the components of the composition in which it is contained or with any components present on or in the body of the individual.

"Physiological conditions" refer to conditions in the body of an animal (e.g., a human). Physiological conditions include, but are not limited to, body temperature and an aqueous environment of physiologic ionic strength, pH and enzymes. Physiological conditions also encompass conditions in the body of a particular subject which differ from the "normal" conditions present in the majority of subjects, e.g., which differ from the normal human body temperature of approximately 37° C. or differ from the normal human blood pH of approximately 7.4.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. The term does not denote a particular age or gender.

The terms "polyethylene glycol", "PEG", "polyethylene oxide" and "PEO" are used interchangeably herein unless indicated otherwise. A CNP variant conjugated via an amino group to a "PEOn" polymer associated with the number n, in general has the formula: $CH_3—[—O—CH_2CH_2—]_n—C(=O)—NHR$, where n is the number of ethylene oxide units and R denotes the rest of the peptide. The "PEOn" polymer can optionally have an alkylene group, $(CH_2)_m$, where m is an integer from 1 to 5, between the carbonyl carbon and the repeating ethylene oxide units. Such a "PEOn" (e.g., PEO12 or PEO24) polymer is monodispersed, i.e., is a single discrete polymer of a particular molecular weight. Similarly, a CNP variant conjugated via an amino group to a "PEGnK" polymer associated with the number nK, in general has the formula: $CH_3—[—O—CH_2CH_2—]_p—C(=O)—NHR$, where p is an integer greater than 1. The "PEGnK" polymer also can optionally have an alkylene group, $(CH_2)_m$, where m is an integer from 1 to 5, between the carbonyl carbon and the repeating ethylene oxide units. However, such a "PEGnK" (e.g., PEG1K, PEG2K, PEG5K or PEG20K) polymer is polydispersed, i.e., contains a mixture of polymers having a distribution of molecular weights, where the number nK denotes the polymer number-average molecular weight ($M_n$) in kilo Daltons. For example, "PEG2K" conjugated to a CNP variant denotes a polydispersed PEG polymer having a polymer number-average molecular weight of around 2 kDa.

When a range of the mass of a polymer (e.g., PEG) is given (e.g., in units of kDa), the range refers to a range of polymer number-average molecular weights, not to a range of molecular weights of multiple polymers in a polydispersed mixture, unless expressly indicated otherwise.

B. CNP Variant Peptides

The use of CNP-22 as a therapeutic is limited by its short half-life in plasma (J. Clin. Endocrinol. Metab., 78: 1428-35 (1994)). In human plasma, the concentration of CNP-22 typically is less than five picomolar. CNP-22 is degraded and cleared from circulation by NEP and NPR-C in humans (Growth Hormone & IGF Res., 16: S6-S14). In all human and animal studies using systemically administered CNP-22, continuous infusion has been used to increase the CNP-22 concentration in the subjects. A CNP peptide having a longer half-life and at least a similar level of functionality would be beneficial to a CNP-based therapeutic strategy. CNP variant peptides having improved properties are disclosed in International Application Nos. WO 2009/067639 and WO 2010/135541 and U.S. Pat. Nos. 8,198,242, 8,598,121, and 8,377,884, all specifically incorporated herein by reference.

In certain embodiments, the CNP variant peptides are derivatives of CNP-37 or CNP-38. The CNP-37 variant peptides can contain amino acid addition(s), deletion(s), and/or substitution(s) with natural or unnatural amino acid(s) or peptidomimetic(s) (e.g., peptide bond isostere(s)) at any one or more of the 37 positions of CNP-37. Non-limiting examples of substitutions that can be made in CNP-37, based on the numbering of CNP-22, include K4R, G5S, G5R, G8S, K10R, G15S, S16Q, M17N, G19R, and combinations thereof.

In one embodiment, the CNP variant peptides are modified CNP-37 or CNP-38 peptides having mutation(s)/substitution(s) at the furin cleavage site, designed to improve in vivo resistance to the furin protease, and/or containing glycine or proline-glycine at the N-terminus, designed to improve plasma stability and prevent pyroglutamine formation. Exemplary CNP-37 variants include but are not limited to:

```
                          [CNP-37(M32N); SEQ ID NO: 1]
QEHPNARKYKGANKKGLSKGCFGLKLDRIGSNSGLGC;

(Met-CNP-37; SEQ ID NO: 2)
MQEHPNARKYKGANKKGLSKGCFGLKLDRIGSMSGLGC;

(Pro-CNP-37; SEQ ID NO: 3)
PQEHPNARKYKGANKKGLSKGCFGLKLDRIGSMSGLGC;

[Gly-CNP-37 (M32N); SEQ ID NO: 4]
GQEHPNARKYKGANKKGLSKGCFGLKLDRIGSNSGLGC;

(Pro-Gly-CNP-37; SEQ ID NO: 5)
PGQEHPNARKYKGANKKGLSKGCFGLKLDRIGSMSGLGC;
```

```
                    -continued
            (Met-Gly-CNP-37; SEQ ID NO: 6)
MGQEHPNARKYKGANKKGLSKGCFGLKLDRIGSMSGLGC;
and (Gly-CNP-37 or CNP-38: SEQ ID NO: 7)
GQEHPNARKYKGANKKGLSKGCFGLKLDRIGSMSGLGC.
```

C. Synthesis and Purification of Cnp Variant Peptides

In some embodiments, the CNP variant peptides useful herein are produced by recombinant expression, using certain techniques known in the art in certain embodiments. See, e.g., Sambrook, Fritsch & Maniatis, Molecular Cloning: A Laboratory Manual, Second Edition. Cold Spring Harbor Laboratory Press (Cold Spring Harbor, N.Y. (1989)); DNA Cloning: A Practical Approach, Volumes I and II, D. N. Glover, Ed. (1985); and Current Protocols in Molecular Biology, John Wiley & Sons, Inc. (1994).

In certain embodiments, the CNP variant peptides are produced by a recombinant process that comprises culturing in a medium a host cell comprising a first polynucleotide encoding a CNP variant peptide linked to a second polynucleotide encoding a cleavable peptide or protein under conditions that result in expression of a fusion polypeptide encoded by the polynucleotides, wherein the fusion polypeptide comprises the CNP variant peptide directly linked to the cleavable peptide or protein or indirectly linked thereto via a linker. In some embodiments, the host cell is transformed with an expression vector comprising the polynucleotide encoding the CNP variant peptide linked to the polynucleotide encoding the cleavable peptide or protein. In certain embodiments, the fusion polypeptide is expressed as a soluble protein or as an inclusion body. The expressed fusion polypeptide can be isolated from the host cell or culture medium, and the isolated fusion polypeptide can be contacted with a cleaving agent to release the CNP variant peptide.

Methods of producing CNP variant peptides are described in U.S. Pat. Nos. 8,198,242, 8,377,884 and 8,598,121, herein incorporated by reference.

Host cells used to produce CNP variant peptides can be bacterial, yeast, insect, non-mammalian vertebrate, or mammalian cells. Bacterial cells include without limitation *E. coli* cell lines and strains. Non-limiting examples of *E. coli* cell lines and strains include BL21, BL21(DE3), BL21 (DE3)pLysS, BL21(DE3)pGro7, ArcticExpress(DE3), C41 [also called C41(DE3)], C43 [also called C43(DE3)], Origami B(DE3), Origami B(DE3)pLysS, KRX, and Tuner (DE3). In an embodiment, CNP variant peptides and CNP fusion proteins are produced using BL21(DE3) cells. Mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), chondrocytes and other bone-derived cells, and precursors of these somatic cell types. Host cells containing the CNP variant DNA or RNA are cultured under conditions appropriate for growth of the cells, expression of the DNA or RNA and identification/selection of cells expressing the CNP variant peptide.

In certain embodiments, the CNP variant peptides are recombinantly expressed as fusion proteins comprising a CNP variant peptide and a cleavable carrier protein or cleavable tag (e.g., peptide tag), wherein the fusion protein comprises the CNP variant peptide directly linked to the cleavable carrier protein or tag or indirectly linked thereto via a linker. Use of a carrier protein or tag facilitates, e.g., detection, isolation and/or purification of the fusion protein. Cleavable carrier proteins and tags include, but are not limited to, histidine (e.g., hexa-His) tags; human transcription factor TAF12 (TAF12), TAF12 fragments, TAF12 histone fold domain, mutants of TAF12 and fragments thereof, TAF12(C/A), TAF12(D/E), TAF12(4D/4E), TAF12(6D/6E), TAF12(10D/10E), TAF12(C/A & D/E), TAF12(C/A & 4D/4E), TAF12(C/A & 6D/6E), TAF12(C/A & 10D/10E); ketosteroid isomerase (KSI); maltose-binding protein (MBP); β-galactosidase (β-Gal); glutathione-S-transferase (GST); thioredoxin (Trx); chitin binding domain (CBD); BMP-2, BMP-2 mutants, BMP-2(C/A); SUMO; and mutants and fragments thereof.

In other embodiments, the CNP variant peptides described herein are synthesized using a peptide synthesizer and purified according to methods known in the art, e.g., according to the methods of Atherton and Sheppard, *Solid Phase Peptide Synthesis: a Practical Approach*, IRL Press (Oxford, England (1989)).

D. Methods of Using Cnp Variant Peptides, Pharmaceutical Compositions of Cnp Variant Peptides, and Routes of Administration Methods of using CNP Variants
Bone Related Disorders/Skeletal Dysplasias Fibroblast growth factors (FGFs) play important roles in bone formation, and mutations in FGF receptor genes (FGFR 1, 2 and 3) give rise to a variety of inherited skeletal malformations (Curr. Biol., 5: 500-507 (1995)). In particular, activating mutations in FGFR-3 are responsible for disorders of the long bones, including achondroplasia, the most common form of human genetic dwarfism (Nature, 371: 252-254 (1994); Cell, 78: 335-342 (1994)), the milder disorder hypochondroplasia (Ann. N.Y. Acad. Sci., 785: 182-187 (1996)), and the more severe and neonatal lethal thanatophoric dysplasia (TD) types I and II (Hum. Mol. Genet., 5: 509-512 (1996); Nat. Genet., 9: 321-328 (1995)). Mouse models overexpressing FGF-2, and consequentially activating FGFR-3, show shortened long bones and macrocephaly (Mol. Biol. Cell, 6: 1861-73 (1995)). Consistent with this model, mice deficient in FGFR-3 show remarkable skeletal overgrowth with wider growth plates (Nature Genet., 12: 390-397 (1996)).

By stimulating matrix production, proliferation and differentiation of chondrocytes and increasing long bone growth, the CNP variant peptides of the disclosure are useful for treating mammals, including humans, suffering from a bone-related disorder, such as a skeletal dysplasia. Non-limiting examples of CNP-responsive bone-related disorders and skeletal dysplasias include achondroplasia, hypochondroplasia, short stature, dwarfism, osteochondrodysplasias, thanatophoric dysplasia, osteogenesis congenita, achondrogenesis, chondrodysplasia congenit, homozygous achondroplasia, chondrodysplasia congenit, camptomelic dysplasia, congenital lethal hypophosphatasia, perinatal lethal type of osteogenesis congenita, short-rib polydactyly syndromes, hypochondroplasia, rhizomelic type of chondrodysplasia congenit, Jansen-type metaphyseal dysplasia, spondyloepiphyseal dysplasia congenital, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia. Further, the CNP variants are useful as an adjunct or alternative to growth hormone for treating idiopathic short stature and other skeletal dysplasias.

In addition, the CNP variant peptides are useful for treating other bone-related conditions and disorders, such as rickets, hypophosphatemic rickets [including X-linked hypophosphatemic rickets (also called vitamin D-resistant rickets) and autosomal dominant hypophosphatemic rickets], and osteomalacia [including tumor-induced osteomalacia (also called oncogenic osteomalacia or oncogenic hypophosphatemic osteomalacia)].

In certain embodiments, the CNP variant peptides and compositions and formulations comprising the same of the present invention are useful for improving one or more of the symptom(s) or physiological consequences of a skeletal dysplasia, wherein the improvement may be increased absolute growth, increased growth velocity, increased qualitative computed tomography (QCT) bone mineral density, improvement in growth plate morphology, increased long bone growth, improvement in spinal morphology, improved elbow joint range of motion and/or decreased sleep apnea. In this regard, it is noted that the terms "improved", "improvement", "increase", "decrease" and grammatical equivalents thereof are all relative terms that when used in relation to a symptom or physiological consequence of a disease state, refer to the state of the symptom or physiological consequence of the disease after treatment with a CNP variant peptide (or composition or formulation comprising the same) of the present invention as compared to the same symptom or physiological consequence of the disease before treatment with a CNP variant peptide (or composition or formulation comprising the same) of the present invention (i.e., as compared to "baseline"). As described above, a "baseline" state can be determined either through measurement of the state in the subject prior to treatment (which can subsequently be compared to the state in the same subject after treatment), or through measurement of that state in a population of subjects suffering from the same affliction that share the same or similar characteristics (e.g., age, sex and/or disease state or progression).

Increasing or Enhancing Growth Velocity

The compositions and formulations of the present invention may also be administered for the purpose of enhancing or increasing growth velocity in a subject suffering from skeletal dysplasia. In a preferred embodiment, the subject suffers from achondroplasia.

Measurements of growth velocity in subjects may be made over time using stardard techniques well known in the art. In certain embodiments, measurements of parameters such as standing height, sitting height, weight, head circumference, upper arm length, lower arm (forearm) length, upper leg length, lower leg length (knee to foot), hand length (wrist to end of finger) and/or foot length may be made over a specified period of time to determine the specific rate of growth as measured by any particular parameter (i.e., the growth velocity). Measurements of growth velocity over a specified period of time may be "annualized", wherein the rate of growth calculated over a specific period of time is converted to the expected rate of growth over a period of one year. Measurements of growth velocity in a subject prior to treatment with a CNP variant peptide of the present invention (i.e., a "baseline" growth velocity) may be compared to measurements of growth velocity during or after treatment with a CNP variant peptide of the present invention to determine the effect of treatment on changes in growth velocity in the subject. A "baseline" growth velocity may also be determined from a population of subjects of the same general age, sex and disease status as the individual being treated with a CNP variant peptide of the present invention.

Improvements in growth velocity as measured by assessment of one of more of the parameters described above (e.g., standing height, etc.) induced or caused by treatment of a subject in need thereof with a CNP variant peptide of the present invention (or composition or formulation comprising the same) may be quantitatively measured. In this regard, in certain embodiments, annualized increase or improvement of growth velocity of any particular parameter in a subject treated with a CNP variant of the present invention (or a composition or formulation comprising the same) are at least about 10%, 15%, 20%, 25%, 30%, 35%, 40%, 45%, or 50%, or more above baseline. In certain embodiments, the methods described herein result in an annualized increase in growth velocity as measured by standing height of at least about 10%, 15%, 20%, 25%, 30%, 35%, 40%, 45%, or 50%, or more above baseline. In other embodiments, the methods described herein result in an annualized increase in growth velocity as measured by either sitting height, weight, head circumference, upper arm length, lower arm (forearm) length, upper leg length, lower leg length (knee to foot), hand length (wrist to end of finger) or foot length of at least about 10%, 15%, 20%, 25%, 30%, 35%, 40%, 45%, or 50%, or more above baseline. As described herein, the baseline comparator may be the annualized growth velocity as measured by the specific parameter prior to treatment of the same subject with a CNP variant peptide of the present invention, or may be the growth velocity determined from a population of subjects of the same general age, sex and disease status as the individual being treated with a CNP variant peptide of the present invention.

Anthropometry data relating to proportionality of certain body segments to others may also be obtained from subjects both before and after treatment with a CNP variant peptide to determine whether administration of a CNP variant peptide results in changes in such proportionality. For example, ratios of upper body length (waist to top of head) to lower body length (waist to foot) may be calculated both prior to treatment with a CNP variant peptide (i.e., baseline) and after treatment with a CNP variant peptide to determine whether treatment with the CNP variant peptide has an adverse effect on body proportionality. Ratios of upper arm to forearm length or upper leg to lower leg (knee to foot) may also be caluculated and compared to determine the effect of CNP variant peptide treatment on body proportionality. In a preferred embodiment of the present invention, administration of a CNP variant peptide to a subject does not result in a significant change in body proportionality as measured by any specific ratio as compared to baseline. In this regard, in certain embodiments, treatment with a CNP variant peptide, or composition or formulation comprising the same, of the present invention results in a change in any of the above described ratios of no more than 0.5, 0.25, 0.20, 0.15, 0.10 or 0.05, preferably no more than 0.05.

In the various methods described herein, it is preferred that administration of the CNP variant peptide or composition or formulation comprising the same not result in an adverse event related to the study drug of grade two or higher, or grade three or higher, in the treated subject. In this regard, techniques for measuring and grading physiological events associated with the treatment of a subject with a compound, and a listing of graded adverse events, can be found at http://evs.nci.nih.gov/ftp1/CTCAE/CTCAE_4.03_2010-06-14_QuickReference_8.5×11.pdf, which is herein incorporated by reference.

Moreover, in the various methods described herein, it is preferred that administration of the CNP variant peptide or composition or formulation comprising the same not result in a clinically significant change (either increase or decrease as compared to baseline) in one or more of the following physiological parameters; blood hemoglobin concentration, blood platelet number, blood electrolyte concentration, blood urea nitrogen concentration, blood creatinine concentration, blood alkaline phosphatase concentration, blood alanine amino transferase concentration or blood aspartate aminotransferase concentration. By "clinically significant change" is meant a change in any one or more of the above parameters that is observed to result in a detectable/observable, adverse physiological change in the subject's overall health.

Pharmaceutical Compositions and Formulations of CNP Variant Peptides

In additional embodiments, the disclosure contemplates use of pharmaceutical compositions and formulations comprising a CNP variant peptide, and one or more pharmaceutically acceptable excipients, carriers and/or diluents. In certain embodiments, the compositions further comprise one or more other biologically active agents (e.g., inhibitors of proteases, receptor tyrosine kinases, and/or the clearance receptor NPR-C).

Non-limiting examples of excipients, carriers and diluents include vehicles, liquids, buffers, isotonicity agents, additives, stabilizers, preservatives, solubilizers, surfactants, emulsifiers, wetting agents, adjuvants, and so on. The compositions can contain liquids (e.g., water, ethanol); diluents of various buffer content (e.g., Tris-HCl, phosphate, acetate buffers, citrate buffers), pH and ionic strength; detergents and solubilizing agents (e.g., Polysorbate 20, Polysorbate 80); anti-oxidants (e.g., methionine, ascorbic acid, sodium metabisulfite); preservatives (e.g., Thimerosol, benzyl alcohol, m-cresol); and bulking substances (e.g., lactose, mannitol, sucrose). The use of excipients, diluents and carriers in the formulation of pharmaceutical compositions is known in the art; see, e.g., Remington's Pharmaceutical Sciences, 18$^{th}$ Edition, pages 1435-1712, Mack Publishing Co. (Easton, Pa. (1990)), which is incorporated herein by reference in its entirety.

For example, carriers include without limitation diluents, vehicles and adjuvants, as well as implant carriers, and inert, non-toxic solid or liquid fillers and encapsulating materials that do not react with the active ingredient(s). Non-limiting examples of carriers include phosphate buffered saline, physiological saline, water, and emulsions (e.g., oil/water emulsions). A carrier can be a solvent or dispersing medium containing, e.g., ethanol, a polyol (e.g., glycerol, propylene glycol, liquid polyethylene glycol, and the like), a vegetable oil, and mixtures thereof.

In some embodiments, the compositions are liquid formulations. In certain embodiments, the formulations comprise a CNP variant peptide in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml, or from about 2 mg/ml to about 10 mg/ml, or about 2 mg/ml or about 10 mg/ml. In other embodiments, the formulation may be a lyophilized formulation or may be a liquid formulation that was previously reconstituted from a lyophilized formulation.

In further embodiments, the compositions comprise a buffer solution or buffering agent to maintain the pH of a CNP-containing solution or suspension within a desired range. Non-limiting examples of buffer solutions include phosphate buffered saline, Tris buffered saline, and Hank's buffered saline. Buffering agents include without limitation sodium acetate, sodium phosphate, citric acid monohydrate and sodium citrate dihydrate. Mixtures of buffering agents can also be used. In certain embodiments, the buffering agent is acetic acid/acetate or citric acid/citrate. The amount of buffering agent suitable in a composition depends in part on the particular buffer used and the desired pH of the solution or suspension. For example, acetate is a more efficient pH buffer at pH 5 than pH 6, so less acetate may be used in a solution at pH 5 than at pH 6. In some embodiments, the buffering agent has a concentration of about 10 mM±5 mM. In certain embodiments, the pH of a composition is from about pH 3 to about pH 7.5, or from about pH 3.5 to about pH 7, or from about pH 3.5 to about pH 6.5, or from about pH 4 to about pH 6, or from about pH 4 to about pH 5, or is at about pH 5.0±1.0, or is at about pH 5.5±1.0.

In other embodiments, the compositions contain an isotonicity agent to render the solution or suspension isotonic and more compatible for injection. Non-limiting examples of isotonicity agents include NaCl, trehalose, mannitol, dextrose, glucose, glycerin, sorbitol, xylitol, and ethanol. In certain embodiments, the isotonicity agent is trehalose or mannitol, which can be employed individually or in combination. In certain embodiments, trehalose or mannitol is in a concentration of about 160±20 mM, or about 140 mM±20 mM, or about 120±20 mM, or about 100 mM±20 mM, or about 80 mM±20 mM, or about 60 mM±20 mM.

In various embodiments, the compositions may comprise a preservative. Preservatives include, but are not limited to, m-cresol and benzyl alcohol. In certain embodiments, the preservative is in a concentration of about 0.4%±0.2%, or about 1%±0.5%, or about 1.5%±0.5%, or about 2.0%±0.5%. In certain embodiments of the invention, the composition or formulation does not contain a preservative.

In various embodiments, the compositions contain an anti-adsorbent agent (e.g., to mitigate adsorption of a CNP variant to glass or plastic). Anti-adsorbent agents include without limitation benzyl alcohol, polysorbate 20, and polysorbate 80. In certain embodiments, the anti-adsorbent is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%.

In various embodiments, the compositions comprise a stabilizer. Non-limiting examples of stabilizers include glycerin, glycerol, thioglycerol, methionine, and ascorbic acid and salts thereof. In some embodiments, when the stabilizer is thioglycerol or ascorbic acid or a salt thereof, the stabilizer is in a concentration from about 0.1% to about 1%.

In various embodiments, the compositions contain an antioxidant. An exemplary anti-oxidant is, without limitation, ascorbic acid. In certain embodiments, the molar ratio of antioxidant to CNP variant peptide is from about 0.1:1 to about 15:1, or from about 1:1 to about 15:1, or from about 0.5:1 to about 10:1, or from about 1:1 to about 10:1 or from about 3:1 to about 10:1.

Pharmaceutically acceptable salts can be used in the compositions, including without limitation mineral acid salts (e.g., hydrochloride, hydrobromide, phosphate, sulfate), salts of organic acids (e.g., acetate, propionate, malonate, benzoate, mesylate, tosylate), and salts of amines (e.g., isopropylamine, trimethylamine, dicyclohexylamine, diethanolamine). A thorough discussion of pharmaceutically acceptable salts is found in Remington's Pharmaceutical Sciences, 18th Edition, Mack Publishing Company, (Easton, Pa. (1990)).

Formulations for parenteral administration can be prepared, e.g., as liquid solutions or suspensions, as solid forms suitable for solubilization or suspension in a liquid medium prior to injection, or as emulsions. For example, sterile injectable solutions and suspensions can be formulated according to techniques known in the art using suitable diluents, carriers, solvents (e.g., buffered aqueous solution, Ringer's solution, isotonic sodium chloride solution), dispersing agents, wetting agents, emulsifying agents, suspending agents, and the like. In addition, sterile fixed oils, fatty esters, polyols and/or other inactive ingredients can be used. As further examples, formulations for parenteral administration include aqueous sterile injectable solutions, which can contain antioxidants, buffers, bacteriostats, and solutes that render the formulation isotonic with the blood of the intended recipient; and aqueous and nonaqueous sterile suspensions, which can contain suspending agents and thickening agents.

Examplary CNP peptide-containing formulations are described in U.S. Pat. Nos. 8,198,242 and 8,598,121. Use of CNP formulations having a pH in the range from about 4 to about 6 is contemplated.

In various embodiments, CNP variant peptides can be formulated in pharmaceutical carriers for administration to subjects affected by skeletal dysplasia. In some embodiments, liquid formulations of CNP variant peptides are formulated according to any combinations of the ingredients and their amounts or concentrations are described below:

| Ingredient Class | Ingredient | Concentration Range |
| --- | --- | --- |
| Active ingredient | CNP variant peptide | 10 mg/mL ± 9.9 mg/mL |
| Buffering agent | Acetic acid/acetate | 10 mM ± 5 mM, or pH 5 ± 1 |
| Buffering agent | Citric acid/citrate | 10 mM ± 5 mM, or pH 5 ± 1 |
| Isotonicity-adjusting agent | NaCl | 140 mM ± 20 mM |
| Isotonicity-adjusting agent | Trehalose; mannitol | 10% ± 5% |
| Preservative | m-Cresol | 0.4% ± 0.1% or 0.2% |
| Preservative/anti-adsorbent | Benzyl alcohol | 1.5% ± 0.5% |
| Stabilizer | Glycerin (glycerol) | 5%-100% (neat) |
| Stabilizer | Methionine | 0.01%-0.2% |
| Stabilizer | Ascorbic acid/ ascorbate salt | 0.1%-1% |
| Stabilizer | Thioglycerol | 0.1%-1% |
| Anti-adsorbent | Polysorbate 20 | 0.001%-0.5% |
| | Polysorbate 80 | 0.001%-0.5% |
| | Benzyl alcohol | 0.5%-1.5% |

Compositions comprising a CNP variant peptide can also be lyophilized formulations. In certain embodiments, the lyophilized formulations comprise a buffer and bulking agent, and optionally an antioxidant. Exemplary buffers include without limitation acetate buffers and citrate buffers. Exemplary bulking agents include without limitation mannitol, sucrose, dexran, lactose, trehalose, and povidone (PVP K24). In certain embodiments, mannitol and/or trehalose is in an amount from about 3% to about 10%, or from about 4% to about 8%, or from about 4% to about 6%. In certain embodiments, sucrose is in an amount from about 6% to about 20%, or from about 6% to about 15%, or from about 8% to about 12%.

In various embodiments, lyophilized formulations of CNP variant peptides are prepared from formulations formulated according to any combinations of the ingredients and their amounts or concentrations described below:

| Ingredient Class | Ingredient | Concentration Range |
| --- | --- | --- |
| Active ingredient | CNP variant | 10 mg/mL ± 9.9 mg/mL |
| Buffering agent | Acetic acid/acetate | 10 mM ± 5 mM, or pH 5 ± 1 |
| Buffering agent | Citric acid/citrate | 10 mM ± 5 mM, or pH 5 ± 1 |
| Isotonicity-adjusting agent/ bulking agent | Sorbitol | 5% ± 3% |
| Isotonicity-adjusting agent/ bulking agent | Mannitol/Trehalose | 5% ± 3% |
| Isotonicity-adjusting agent/ bulking agent | Sucrose | 10% ± 5% |
| Preservative | m-Cresol | 0.4% ± 0.2% |
| Preservative/anti-adsorbent | Benzyl alcohol | 1.5% ± 0.5% |
| Stabilizer | Glycerin (glycerol) | 5%-100% (neat) |
| Stabilizer | Methionine | 0.01%-0.2% |
| Stabilizer | Ascorbic acid/ ascorbate salt | 0.1%-1% |
| Stabilizer | Thioglycerol | 0.1%-1% |
| Anti-adsorbent | Polysorbate 20 | 0.001%-0.5% |
| | Polysorbate 80 | 0.001%-0.5% |
| | Benzyl alcohol | 0.5%-1.5% |

In various embodiments, a formulation comprising a CNP variant peptide has a pH of about 3-7, or about 3-6, or about 3.5-6.5, or about 4-6, or about 4-5, or about 4.5-5.5. In some embodiments, for pH 4-5.5 a suitable buffering agent is acetic acid/acetate (e.g., sodium acetate), and for pH 5.5-6 a suitable buffering agent is citric acid/citrate. Citric acid/citrate (e.g., sodium citrate) is also a suitable buffering agent in the range of pH 3-6 or pH 4-6. In certain embodiments, the buffering agent has a concentration in the formulation of about 2-50 mM, or about 2-40 mM, or about 2-30 mM, or about 5-30 mM, or about 2-20 mM, or about 5-20 mM, or about 5-15 mM.

Also to minimize or avoid deamidation of a CNP variant peptide, water can be removed from the formulation by lyophilization. In some embodiments, lyophilized formulations contain any combinations of the following components: buffer: sodium acetate and acetic acid, or sodium citrate and citric acid; isotonicity/bulking agent: mannitol (e.g., 3-10%, 2-8% or 4-6%); sucrose (e.g., 6-20%, 5-15% or 8-12%); antioxidants: methionine and/or ascorbic acid with molal ratio of each antioxidant to CNP variant peptide from about 0.1:1 to about 1:1, or from about 0.5:1 to about 5:1, or from about 1:1 to about 15:1, or from about 1:1 to about 10:1, or from about 3:1 to about 10:1.

Deamidation can also be minimized or avoided by storing a CNP composition (e.g., a liquid formulation or a lyophilized formulation) at lower temperature, such as at about 5° C., 0° C., −10° C., −20° C., −30° C., −40° C., −50° C., −60° C., −70° C., −80° C., −90° C., or −100° C.

To minimize or avoid oxidation of oxidizable residues (e.g., methionine) in a CNP variant peptide, the variant can be formulated with one or more antioxidants. Exemplary antioxidants include, but are not limited to, methionine, ascorbic acid, and thioglycerol. Oxidation of, e.g., methionine residues can also be minimized or prevented by purging oxygen from a liquid medium (if a liquid formulation) with nitrogen or argon, and/or by purging oxygen from a container or packaging with nitrogen or argon.

In some embodiments, to minimize or prevent adsorption (e.g., adsorption of a CNP variant peptide to plastic or glass), polysorbate 20, polysorbate 80 or benzyl alcohol, or a combination thereof, is added to a CNP formulation. In certain embodiments, each of the anti-adsorbent(s) is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%. Exemplary range(s) of anti-adsorbent(s) in the formulation include without limitation from about 0.001% to about 0.5% of Polysorbate 20, from about 0.001% to about 0.5% of Polysorbate 80, and/or from about 0.5% to about 1.5% of benzyl alcohol The disclosure also provides kits containing, e.g., bottles, vials, ampoules, tubes, cartridges and/or syringes that comprise a liquid (e.g., sterile injectable) formulation or a solid (e.g., lyophilized) formulation. The kits can also contain pharmaceutically acceptable vehicles or carriers (e.g., solvents, solutions and/or buffers) for reconstituting a solid (e.g., lyophilized) formulation into a solution or suspension for administration (e.g., by injection), including without limitation reconstituting a lyophilized formulation in a syringe for injection or for diluting concentrate to a lower concentration. Furthermore, extemporaneous injection solutions and suspensions can be prepared from, e.g., sterile powder, granules, or tablets comprising a CNP-containing composition. The kits can also include dispensing devices, such as aerosol or injection dispensing devices, pen injectors, autoinjectors, needleless injectors, syringes, and/or needles.

Dosages and Frequency of Dosing

As used herein, the term "therapeutically effective amount" of an active agent (e.g., a CNP variant peptide) refers to an amount that provides therapeutic benefit to a patient. The amount may vary from one individual to another and may depend upon a number of factors, including the overall physical condition of the patient. A therapeutically effective amount of a CNP variant peptide can be readily ascertained by one skilled in the art, using publicly available materials and procedures. For example, the amount of a CNP variant peptide used for therapy should give an acceptable rate of growth based on growth charts for children ages 0-17 years with achondroplasia (214 females and 189 males), which list height for age, head circumference, and segmental growth (Horton W A et al., Standard growth curves for achondroplasia, J. Pediatr., 93: 435-8 (1978)). CDC charts can be used to assess weight for age and weight for height or BMI for age. Secondary outcomes with courses that are more chronic in nature can also be measured.

The dosing frequency for a particular individual may vary depending upon various factors, including the disorder being treated and the condition and response of the individual to the therapy. In certain embodiments, a pharmaceutical composition containing a CNP variant peptide is administered to a subject about one time per day, one time per two days, one time per three days, or one time per week, twice per week, three times per week, once every two weeks, or monthly. In one embodiment, for treatment of bone-related disorders (e.g., skeletal dysplasias, including achondroplasia), a daily or weekly dose of a CNP variant peptide is administered to patients until and/or through adulthood.

In certain embodiments, the CNP variant peptides described herein are administered at a dose in the range from about 5 or 10 nmol/kg to about 300 nmol/kg, or from about 20 nmol/kg to about 200 nmol/kg. In some embodiments, the CNP variant peptides are administered at a dose of about 5, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg or other dose deemed appropriate by the treating physician. In other embodiments, the CNP variant peptides are administered at a dose of about 5, 7.5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 1000 µg/kg, or about 1, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. In various embodiments, the CNP variant peptide is administered at a dose from about 7.5 to 100 µg/kg, or from about 15 to 75 µg/kg, or about 15 to 30 µg/kg, or about 2.5 µg/kg, 7.5 µg/kg, 15.0 µg/kg, 30.0 µg/kg or 60.0 µg/kg. The doses of CNP variant peptides described herein can be administered according to the dosing frequency/ frequency of administration described herein, including without limitation daily, 2 or 3 times per week, weekly, every 2 weeks, every 3 weeks, monthly, etc. Administration of a CNP variant peptide may occur over an extended period of time, in some cases, over one month, three months, six months or more.

The frequency of dosing/administration of a CNP variant peptide for a particular subject may vary depending upon various factors, including the disorder being treated and the condition and response of the subject to the therapy. The CNP variant peptide can be administered in a single dose or in multiple doses per dosing. In certain embodiments, the CNP variant peptide is administered, in a single dose or in multiple doses, daily, every other day, every 3 days, 2 times per week, 3 times per week, weekly, bi-weekly, every 3 weeks, monthly, every 6 weeks, every 2 months, every 3 months, or as deemed appropriate by the treating physician.

In some embodiments, a CNP variant peptide is administered so as to allow for periods of growth (e.g., chondrogenesis), followed by a recovery period (e.g. osteogenesis). For example, the CNP variant peptide may be administered intravenously, subcutaneously, intraarticularly or by another mode daily or multiple times per week for a period of time, followed by a period of no treatment, then the cycle is repeated. In some embodiments, the initial period of treatment (e.g., administration of the CNP variant peptide daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the CNP variant peptide is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

Modes of Administration

The CNP variant peptides, or pharmaceutical compositions or formulations comprising them, can be administered to subjects in various ways such as, e.g., by injection subcutaneously, intraarticularly, intravenously, intra-arterially, intraperitoneally, intramuscularly, intradermally, or intrathecally. In one embodiment, the CNP variant peptides are administered by a single subcutaneous, intraarticular, intravenous, intra-arterial, intraperitoneal, intramuscular, intradermal or intrathecal injection once a day, one every other day, once every three days, or once a week.

The CNP variant peptides can also be administered by direct injection at or near the site of disease. Further, the CNP variant peptides can be administered by implantation of a depot at the target site of action (e.g., an abnormal or degeneratied joint or cartilage area). Alternatively, the CNP variant peptides can be administered sublingually under the tongue (e.g., sublingual tablet) or by inhalation into the lungs (e.g., inhaler or aerosol spray), by delivery into the nasal cavity (e.g., intranasal spray), by delivery into the eye (e.g., eye drop), or by transdermal delivery (e.g., by means of a patch on the skin). The CNP variant peptides may also be administered orally in the form of microspheres, microcapsules, liposomes (uncharged or charged (e.g., cationic)), polymeric microparticles (e.g., polyamides, polylactide, polyglycolide, poly(lactide-glycolide)), microemulsions, and the like.

A further method of administration is by osmotic pump (e.g., an Alzet pump) or mini-pump (e.g., an Alzet mini-osmotic pump), which allows for controlled, continuous and/or slow-release delivery of the CNP variant peptide or pharmaceutical composition over a pre-determined period. The osmotic pump or mini-pump can be implanted subcutaneously, or near the target site (e.g., the long bones of limbs, the epiphyses, etc.).

It will be apparent to one skilled in the art that the CNP variant peptides or compositions thereof can also be administered by other modes. Determination of the most effective mode of administration of the CNP variant peptides or compositions thereof is within the skill of the skilled artisan Additional aspects and details of the disclosure will be apparent from the following examples, which are intended to be illustrative rather than limiting.

E. EXAMPLES

Example 1—Six Month Human Clinical Trial Data for Achondroplasia Patients

In order to determine the effect of CNP variant peptides on symptoms of skeletal dysplasia, such as achondroplasia, and on long bone growth and/or growth velocity (as measured by the rate of increase in the patient's standing height post-treatment as compared to pre-treatment) in achondroplasia patients, dose escalation studies were carried out in achonsdroplaisa (ACH) children 5-14 years old (inclusive) who have documented ACH, as documented by clinical grounds and confirmed by genetic testing.

Prior to administration of a formulation comprising a CNP variant peptide as described herein, serial growth measurements (on a variety of different parameters) and growth velocity rate measurements (in at least patient standing height) were collected at three month intervals from untreated study patients to establish baseline levels for growth velocity and body proportionality ratios as described above. Once baseline levels for growth velocity and body proportionality ratios were obtained, a formulation comprising a CNP variant peptide (specifically Pro-Gly-CNP-37; SEQ ID NO: 5) was then administered as a daily dose subcutaneously in one of the following daily dosing regimens: Cohort 1 (n=8): daily dose of 2.5 µg/kg of Pro-Gly-CNP-37 peptide, Cohort 2 (n=8), daily dose of 7.5 µg/kg of Pro-Gly-CNP-37 peptide; Cohort 3 (n=10), daily dose of 15.0 µg/kg of Pro-Gly-CNP-37 peptide. Daily subcutaneous administration was carried out for 6 months.

More specifically, Pro-Gly-CNP-37 peptide was formulated into a sterile, preservative-free composition comprising either 2.0 mg/ml or 10 mg/ml of the CNP peptide in combination with 0.28 mg/ml citric acid monohydrate, 1.08 mg/ml sodium citrate dihydrate, 58.01 mg/ml trehalose dihydrate, 15 mg/ml D-mannitol, 0.73 mg/ml L-methionine and 0.05 mg/ml polysorbate 80, pH 5.5. This liquid composition was reconstituted from an originally lyophilized formulation comprising the described components and was supplied in a sterile, single use, type I untreated borosilicate clear glass vial. This reconstituted liquid formulation was employed in all human clinical treatment studies described herein.

During the course of administration of the CNP variant peptide, various assessments were taken, including body weight, measurement of bone length and bone growth, including calculating upper arm length to forearm length ratio, upper leg length to lower leg length ratio, and upper body length to lower body length ratio. Growth velocity measurements were also calculated by measuring standing height of the patients, and the data was compared to the baseline growth velocity rates previously obtained. Assessments were taken at approximately days 15, 22, 29, 43, 85, 127 and 183 after first administration of the CNP variant peptide.

Exploratory imaging assessment data included measurements and morphology of the spine, long bones and extremities, as well as measures of growth plate, bone age, and bone mineral density. Assays include anterior-posterior (AP) x-ray of pelvis for baseline hip assessment; posterior-anterior (PA) radiographs of the left hand and wrist to assess bone age (Greulich, 1971, Stanford University Press.); (Tanner, 1975, Academic Press.), growth plates, hand length, and cortical thickness; AP lower extremity radiograph to assess growth plates, tibial length, cortical thickness, and bowing, AP radiographs of lumbar spine to assess transverse interpedicular distance. Lateral radiographs of lumbar spine to assess thoracolumbar lordosis angle, vertebral morphology, as well as other potential changes related to spinal stenosis, QCT scan of forearm and tibia to assess bone mineral density, growth plate morphology, and bone length are performed. This scan can be acquired with a standard CT scanner, calibration phantom, and designated software, using a predetermined low radiation dose protocol, which avoids direct radiation to the head and torso.

Sleep study: Untreated sleep apnea in childhood has been repeatedly associated with poor functional and health outcomes, including negative impacts on certain aspects of child development such as behavior and learning. Cognitive deficits reported to be associated with sleep apnea in children include learning, memory, and visual-spatial skills; language, verbal fluency, school performance and executive functions. In addition, pediatric sleep-disordered breathing has been associated with growth abnormalities; alterations in cardiac health, including both systolic and diastolic blood pressure, autonomic regulation, brain oxygenation, and cerebral blood flow, suggesting that childhood obstructive sleep apnea syndrome may jeopardize long-term cardiovascular health; and systemic markers of inflammation (Marcus, 2012, Pediatrics). A sleep-testing device is used to assess the presence and severity of sleep-disordered breathing by measurement of blood oxygen saturation, pulse rate, and airflow during overnight monitoring. Assessment of sleep apnea includes, but is not limited to, determining the number of episodes of apnea and hypopnea per hour (Apnea/Hypopnea Index, AHI).

Flexion-extension measures of elbow joint range of motion are measured with a goniometer.

Biomarkers are evaluated by change from baseline and include, but are not limited to, assessment for cartilage turnover (CTX-II), chondrocyte and osteoblast activity (bone-specific alkaline phosphatase), bone formation (P1NP), bone turnover (osteocalcin); and markers of CNP bioactivity (cGMP, NT-proCNP, and ANP) as well as additional biomarkers. Samples for blood and urine biochemical markers of collagen and bone turnover, and for markers of CNP activity, are collected at the designated time points.

Results: Change in growth velocity as a result of treatment with the CNP variant peptide Pro-Gly-CNP-37 was measured in Cohort 1 (2.5 µg/kg/day), Cohort 2 (7.5 µg/kg/day) and Cohort 3 (15 µg/kg/day) for a total of 26 patients by measuring changes in standing height during treatment and comparing to the baseline growth velocity rates measured prior to treatment. Average change in standing height growth velocity over the 6 month study is summarized in Table 1. As demonstrated in Table 1, no significant increase in growth velocity was observed in the achondroplasia patients treated with 2.5 µg/kg/day of Pro-Gly-CNP-37 for 6 months (cohort 1). In contrast to the patients in cohort 1, however, achondroplasia patients treated with 7.5 µg/kg/day of Pro-Gly-CNP-37 for 6 months (cohort 2) demonstrated a statistically significant increase (p value=0.04) in standing height growth velocity (as compared to their previously calculated baseline standing height growth velocity rate). More specifically, the patients in cohort 2 showed a mean increase in standing height growth velocity of 1.3 cm/year, which represented an increase in annualized growth velocity of 45% above baseline. Finally, achondroplasia patients treated with 15 µg/kg/day of Pro-Gly-CNP-37 for 6 months (cohort 3) also demonstrated a statistically significant increase (p value=0.01) in standing height growth velocity (as compared to their previously calculated baseline standing height growth velocity rate). More specifically, the patients in cohort 3 showed a mean increase in standing height growth velocity of 2.0 cm/year, which represented an increase in annualized growth velocity of 50% above baseline. These data demonstrate that daily subcutaneous treatment of achondroplasia patients with at least 7.5 µg/kg of a CNP variant peptide for a period of 6 months or greater has a beneficial effect on bone growth, growth velocity and generally treating symptoms of achondroplasia.

TABLE 1

Efficacy Analysis: Annualized 6-Months Growth Velocity

| Growth Velocity | Cohort 1<br>2.5 µg/kg/daily<br>(n = 8*) | Cohort 2<br>7.5 µg/kg/daily<br>(n = 8) | Cohort 3<br>15 µg/kg/daily<br>(n = 10) |
| --- | --- | --- | --- |
| Baseline | | | |
| Mean (cm/Year) | 3.8 | 2.9 | 4.0 |
| Post-Treatment | | | |
| Mean (cm/year)<br>Change from Baseline | 3.4 | 4.2 | 6.1 |
| Mean (cm/year) | −0.4 | 1.3 | 2.0 |
| 95% Confidence<br>Interval (cm/year) | −1.8, 1.1 | 0.1, 2.5 | 0.6, 3.4 |
| p-value** | 0.56 | 0.04 | 0.01 |
| Percent Increase<br>from Baseline | | | |
| Based on means (%) | NM | 45 | 50 |

Body proportionality. Body proportionality ratios (upper body length to lower body length, upper arm length to forearm length, and upper leg length to lower leg [knee to foot] length) were calculated for all patients in all cohorts both prior to treatment (baseline) and during the course of treatment with the CNP variant peptide.

For cohort 1, the mean baseline upper body length to lower body length ratio, the mean baseline upper arm length to forearm length ratio, and the mean baseline upper leg length to lower leg length ratio was 2.09, 1.13 and 0.67, respectively. After 6 months of daily subcutaneous treatment with 2.5 µg/kg of the CNP variant peptide, the same body proportion ratios were determined to be 2.07, 1.11 and 0.67, respectively, representing mean changes in those same body proportion ratios of −0.02, −0.02 and 0.0, respectively.

For cohort 2, the mean baseline upper body length to lower body length ratio, the mean baseline upper arm length to forearm length ratio, and the mean baseline upper leg length to lower leg length ratio was 2.03, 1.14 and 0.66, respectively. After 6 months of daily subcutaneous treatment with 7.5 µg/kg of the CNP variant peptide, the same body proportion ratios were determined to be 2.03, 1.14 and 0.66, respectively, representing mean changes in those same body proportion ratios of 0.0, 0.0 and 0.0, respectively.

For cohort 3, the mean baseline upper body length to lower body length ratio, the mean baseline upper arm length to forearm length ratio, and the mean baseline upper leg length to lower leg length ratio was 1.91, 1.13 and 0.69, respectively. After 6 months of daily subcutaneous treatment with 15 µg/kg of the CNP variant peptide, the same body proportion ratios were determined to be 1.89, 1.08 and 0.69, respectively, representing mean changes in those same body proportion ratios of −0.02, −0.05 and 0.0, respectively.

These data demonstrate that treatment of achondroplasia patients with a CNP variant peptide has no significant adverse effect on overall body proportionality, as all measured body proportionality ratio changes fell between −0.05 and 0.05, relative to baseline, after 6 months of treatment with the CNP variant peptide.

Adverse events. All patients in each of the above described cohorts were regularly assessed for the presence of adverse events (as defined by http://evs.nci.nih.gov/ftp1/CTCAE/CTCAE_4.03_2010-06-14_QuickReference_8.5× 11.pdf) specifically caused by treatment with the CNP variant peptide. No patient in any of the three study cohorts evidenced an adverse event of grade two or higher that was determined to be related to the study drug, demonstrating that treatment of achondroplasia patients with CNP variant peptides does not result in serious adverse physiological events.

Moreover, all patients in each study cohort were regularly monitored for blood hemoglobin concentration, blood platelet number, blood electrolyte concentration, blood urea nitrogen concentration, blood creatinine concentration, blood alkaline phosphatase concentration, blood alanine amino transferase concentration and blood aspartate aminotransferase concentration. The data obtained from each of the three study cohorts demonstrated that no clinically significant changes in any of the above described safety indicators were observed, again confirming underlying safety for CNP variant peptide therapy for achondroplasia and associated symptoms.

Example 2—Twelve Month Human Clinical Trial Data for Achondroplasia (Cohort 3)

Following the first 6-month clinical trial treatment and assessment period, the 10 achondroplasia patients from cohort 3 described in Example 1 above were continued on the clinical regime of 15 µg/ml of Pro-Gly-CNP-37 administered subcutaneously daily for an additional 6 months (12 months total). During the course of the additional six month treatment period, various assessments were taken, including body weight, measurement of bone length and bone growth, including calculating upper arm length to forearm length ratio, upper leg length to lower leg length ratio, and upper body length to lower body length ratio. Growth velocity measurements were also calculated by measuring standing height of the patients, and the data was compared to the baseline growth velocity rates previously obtained.

Results: Change in growth velocity as a result of treatment for 12 months with the CNP variant peptide Pro-Gly-CNP-37 was measured in Cohort 3 (15 µg/kg/day) for a total of 10 patients by measuring changes in standing height during treatment and comparing to the baseline growth velocity rates measured prior to treatment. The data obtained from this 12-month study demonstrated that achondroplasia patients treated with 15 µg/kg/day of Pro-Gly-CNP-37 for 12 months (cohort 3) demonstrated a statistically significant increase (p value=0.017) in standing height growth velocity (as compared to their previously calculated baseline standing height growth velocity rate). More specifically, the patients in cohort 3 showed a mean increase in standing height growth velocity of 1.9 cm/year, which represented an increase in annualized growth velocity of more than 47% above baseline. These data demonstrate that daily subcutaneous treatment of achondroplasia patients with at least 15 µg/kg of a CNP variant peptide for a period of 12 months or greater has a beneficial effect on bone growth, growth velocity and generally treating symptoms of achondroplasia.

Body proportionality. Body proportionality ratios (upper body length to lower body length, upper arm length to forearm length, and upper leg length to lower leg [knee to foot] length) were calculated for the 10 patients in cohort 3 both prior to treatment (baseline) and during the course of treatment with the CNP variant peptide.

For cohort 3, the mean baseline upper body length to lower body length ratio, the mean baseline upper arm length to forearm length ratio, and the mean baseline upper leg length to lower leg length ratio was 1.91, 1.13 and 0.69, respectively. After 6 months of daily subcutaneous treatment with 15 µg/kg of the CNP variant peptide, the same body proportion ratios were determined to be 1.88, 1.16 and 0.69, respectively, representing mean changes in those same body proportion ratios of −0.03, 0.03 and 0.0, respectively.

These data demonstrate that treatment of achondroplasia patients with a CNP variant peptide has no significant adverse effect on overall body proportionality, as all measured body proportionality ratio changes fell between −0.05 and 0.05, relative to baseline, after 12 months of treatment with the CNP variant peptide.

Adverse events. All patients in cohort 3 were regularly assessed for the presence of adverse events (as defined by http://evs.nci.nih.gov/ftp1/CTCAE/CTCAE_4.03_2010-06-14_QuickReference_8.5×11.pdf) specifically caused by treatment with the CNP variant peptide during the course of treatment. No patient in cohort 3 evidenced an adverse event of grade two or higher that was determined to be related to the study drug, demonstrating that treatment of achondroplasia patients with CNP variant peptides does not result in serious adverse physiological events.

Moreover, all patients in cohort 3 were regularly monitored for blood hemoglobin concentration, blood platelet number, blood electrolyte concentration, blood urea nitrogen concentration, blood creatinine concentration, blood alkaline phosphatase concentration, blood alanine amino transferase concentration and blood aspartate aminotransferase concentration. The data obtained from this study demonstrated that no clinically significant changes in any of the above described safety indicators were observed, again confirming underlying safety for CNP variant peptide therapy for achondroplasia and associated symptoms.

Based upon the human clinical data described above, daily subcutaneously administered doses of 30 µg/kg/day and 60 µg/kg/day of Pro-Gly-CNP-37 to human achondroplasia patients will also be tested for efficacy and safety as described above. Based upon the data disclosed herein, it is fully expected that such administration regimes will provide both efficacious and safe for the treatment of achondroplasia in human patients.

Numerous modifications and variations to the disclosure, as set forth in the embodiments and illustrative examples described herein, are expected to occur to those skilled in the art. Consequently only such limitations as appear in the appended claims should be placed on the disclosure.

What is claimed is:

1. A method of treating skeletal dysplasia in a subject comprising the step of administering to said subject a composition comprising a CNP variant peptide in an amount of at least 7.5 µg/kg of said CNP variant peptide, wherein the CNP variant peptide is selected from the group consisting of:

```
                             [CNP-37(M32N); SEQ ID NO: 1]
QEHPNARKYKGANKKGLSKGCFGLKLDRIGSNSGLGC;

(Met-CNP-37; SEQ ID NO: 2)
MQEHPNARKYKGANKKGLSKGCFGLKLDRIGSMSGLGC;

(Pro-CNP-37; SEQ ID NO: 3)
PQEHPNARKYKGANKKGLSKGCFGLKLDRIGSMSGLGC;

[Gly-CNP 37(M32N); SEQ ID NO: 4]
GQEHPNARKYKGANKKGLSKGCFGLKLDRIGSNSGLGC;

(Pro-Gly-CNP-37; SEQ ID NO: 5)
PGQEHPNARKYKGANKKGLSKGCFGLKLDRIGSMSGLGC;

(Met-Gly-CNP-37; SEQ ID NO: 6)
MGQEHPNARKYKGANKKGLSKGCFGLKLDRIGSMSGLGC;
and (Gly-CNP-37: SEQ ID NO: 7)
GQEHPNARKYKGANKKGLSKGCFGLKLDRIGSMSGLGC,
``` wherein said composition comprises a formulation comprising citric acid monohydrate, sodium citrate dihydrate, trehalose dihydrate, D-mannitol, L-methionine and polysorbate 80, and wherein the step of administering treats said skeletal dysplasia.

2. The method of claim 1, wherein the treatment results in an improvement in one or more symptoms of skeletal dysplasia selected from the group consisting of increased absolute growth, increased growth velocity, increased QCT bone mineral density (BMD), improvement in growth plate morphology, increased long-bone growth, improvement in morphology of the spine, improved elbow joint range of motion and decreased sleep apnea.

3. The method of claim 1 wherein the skeletal dysplasia is selected from the group consisting of achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, chondrodysplasia punctata, camptomelic dysplasia, congenital lethal hypophosphatasia, perinatal lethal type of osteogenesis imperfecta, short-rib polydactyly syndromes, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia and spondyloepimetaphyseal dysplasia.

4. The method of claim 1, wherein said composition is administered once daily.

5. The method of claim 4, wherein said composition is administered once daily over a period of at least 6 months.

6. The method of claim 1, wherein said composition is administered subcutaneously.

7. The method of claim 1 comprising administering said composition comprising said CNP variant peptide to said subject in an amount of at least about 15 µg/kg per day of said CNP variant peptide.

8. The method of claim 1, wherein the formulation is lyophilized, is in liquid form, or is reconstituted from a lyophilized formulation.

9. The method of claim 1, wherein the formulation comprises at least about 2.0 mg/ml of the CNP peptide variant.

10. The method of claim 1, wherein, in the formulation, citric acid monohydrate is present at a concentration of from about 0.15 mg/ml to about 0.40 mg/ml, sodium citrate dihydrate is present at a concentration of from about 0.5 mg/ml to about 1.5 mg/ml, trehalose dihydrate is present at a concentration of from about 30 mg/ml to about 70 mg/ml, D-mannitol is present at a concentration of from about 10 mg/ml to about 20 mg/ml, L-methionine is present at a concentration of from about 0.5 mg/ml to about 1.5 mg/ml and polysorbate 80 is present at a concentration of from about 0.01 mg/ml to about 0.1 mg/ml.

11. The method of claim 1, wherein, in the formulation, citric acid monohydrate is present at a concentration of about 0.28 mg/ml, sodium citrate dihydrate is present at a concentration of about 1.08 mg/ml, trehalose dihydrate is present at a concentration of about 58.01 mg/ml, D-mannitol is present at a concentration of about 15 mg/ml, L-methionine is present at a concentration of about 0.73 mg/ml and polysorbate 80 is present at a concentration of about 0.05 mg/ml.

12. The method of claim 1, wherein the formulation is preservative-free.

13. The method of claim 1, wherein the formulation has a pH of between about 5.0 and about 6.0.

* * * * *

UNITED STATES PATENT AND TRADEMARK OFFICE
CERTIFICATE OF CORRECTION

Page 1 of 1

PATENT NO. : 10,646,550 B2
APPLICATION NO. : 15/880002
DATED : May 12, 2020
INVENTOR(S) : Sherry Bullens et al.

It is certified that error appears in the above-identified patent and that said Letters Patent is hereby corrected as shown below:

In the Claims

At Column 34, Lines 26-27, "chondrodysplasia punctata, camptomelic dysplasia," should be -- campomelic dysplasia, --.

At Column 34, Lines 38-39, "metatrophic dysplasia" should be -- metatropic dysplasia --.

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*